(12) United States Patent
Hung

(10) Patent No.: US 7,132,232 B2
(45) Date of Patent: Nov. 7, 2006

(54) IDENTIFICATION OF VIRAL AGENTS IN BREAST DUCTS AND ANTIVIRAL THERAPY THEREFORE

(75) Inventor: David Hung, Belmont, CA (US)

(73) Assignee: Cytyc Corporation, Marlborough, MA (US)

( * ) Notice: Subject to any disclaimer, the term of this patent is extended or adjusted under 35 U.S.C. 154(b) by 110 days.

(21) Appl. No.: 09/923,791

(22) Filed: Aug. 8, 2001

(65) Prior Publication Data

US 2002/0045162 A1    Apr. 18, 2002

Related U.S. Application Data

(60) Provisional application No. 60/223,857, filed on Aug. 8, 2000.

(51) Int. Cl.
  C12Q 1/70    (2006.01)
  A61K 39/00   (2006.01)
  G01N 33/53   (2006.01)
  G01N 33/574  (2006.01)

(52) U.S. Cl. ............... 435/5; 424/184.1; 435/5; 435/7.1; 435/7.23

(58) Field of Classification Search ............. 424/184.1; 435/5, 7.1, 7.23
  See application file for complete search history.

(56) References Cited

U.S. PATENT DOCUMENTS

| 5,169,774 | A  | 12/1992 | Frankel et al. |
| 5,677,171 | A  | 10/1997 | Hudziak et al. |
| 5,720,937 | A  | 2/1998  | Hudziak et al. |
| 5,725,856 | A  | 3/1998  | Hudziak et al. |
| 5,763,415 | A  | 6/1998  | Sukumar |
| 6,221,622 | B1 | 4/2001  | Love |
| 6,413,228 | B1 | 7/2002  | Hung et al. |

FOREIGN PATENT DOCUMENTS

| EP | 0 502 485 B1 | 10/1996 |
| WO | WO 99-55384  | 11/1999 |
| WO | WO 00 42841  | 7/2000 |
| WO | WO 00 51666  | 9/2000 |

OTHER PUBLICATIONS

Androphy E.J. Papillomaviruses and interferon. Ciba Foundation Symposium (1986) vol. 120, pp. 221-234.*
Noguchi et al. Clonal analysis of solitary intraductal papilloma of the breast by means of polymerase chain reaction. American Journal of Pathology (1994) vol. 144, No. 6, pp. 1320-1325.*
Gross G. Therapy of human papillomavirus infection and assoicated epithelial tumors. Intervirology (1997) vol. 40, pp. 368-377.*
Evron et al. Detection of breast cancer cells in ductal lavage fluid by methylation-specific PCR. The Lancet (Apr. 2001) vol. 35 pp. 1335-1336.*

HPV33 DNA In Premalignant and Malignant Breast Lesions in Chinese and Japanese Populations, Anticancer Research, Nov. 1999, pp. 5057-5062, vol. 19, No. 6B, XP001022307.
G.J. Hammons, "Increased expression of hepatic DNA methyltransferase in smokers", Cell Biol Toxicol, 1999; 15(6), pp. 389-394, Abstract Only.
F.E. Domann et al., "Epigenetic silencing of maspin gene expression in human breast cancers", Int. J. Cancer, Mar. 15, 2000; 85(6), pp. 805-810, Abstract Only.
B.K. Nayak et al, "Mutation and methylation status of p53 gene promoter in human breast tumours", Tumour Biol. Nov.-Dec./1999, 20(6), pp. 341-346, Abstract Only.
Y.I. Kim, "Folate and cancer prevention: a new medical application of folate beyond hyperhomocysteinemia and neural tube defects", Nutr. Rev., Oct. 1999, 57(10), pp. 314-321, Abstract Only.
S.J. Nass et al., "Expression of DNA methyl-transferase (DMT) and the cell cycle in hman breast cancer cells", Oncogene, Dec. 9, 1999, 18(52) pp. 7453-7461, Abstract Only.
M. Esteller, "Epigenetic lesions causing genetic lesions in human cancer. promoter hypermethylation of DNA repair genes", Eur J Cancer, Dec. 2000, 36(18), pp. 2294-2300, Abstract Only.
S.S. Dehal et al., "The aromatase inactivator 4-hydroxyandrostenedione (4-OH-A) inhibits tamoxifen metabolism by rat hepatic cytochrome P-450 3A: potential for drug-drug interaction of tamoxifen and 4-OH-A in combined anti-breast cancer therapy", Drug Metab Dispos, Mar. 1999, 27(3), pp. 389-394, Abstract Only.
Leborgne, Intraductal Biopsy of Certain Pathologic Processes of the Breast, Surgery 19:47-54 (1946).
Papanicolaou et al., Exfoliative Cytology of the Human Mammary Gland and Its Value in the Diagnosis of Cancer and Other Diseases of the Breast, Cancer 11:377-409 (1958).
Buehring, Screening for Breast Atypias Using Exfoliative Cytology, Cancer 43(5):1788-1799 (1979).
Makita et al., Duct Endoscopy and Endoscopic Biopsy in the Evaluation of Nipple Discharge, Breast Cancer Research and Treatment 18:179-188 (1991).
Jin et al., Study of Tumor Markers in Mammary Ductal Lavage for Early Detection of Breast Carcinoma, Zhongguo Zhong Liu Lin Chuang 23(6):381-385 (1996), with English translation.
Love et al., Breast-Duct Endoscopy to Study Stages of Cancerous Breast Disease, Lancet 348:997-999 (1996).
Sauter et al., Nipple Aspirate Fluid: A Promising Non-Invasive Method to Identify Cellular Markers of Breast Cancer Risk, British J. Cancer 76(4):494-501 (1997).
M. Widschwendter et al., "Methylation and silencing of the retinoic acid receptor-beta2 gene in breast cancer", J. National Cancer Institute, May 17, 2000; 92(10), pp. 826-832, Abstract Only.
K.E. Conway et al., "TMS1, a novel proapoptotic caspase recruitment domain protein, is a target of methylation-induced gene silencing in human breast cancers", Cancer Research, Nov. 15, 2000, 60(22), pp. 6236-6242, Abstract Only.

(Continued)

Primary Examiner—Ulrike Winkler
(74) Attorney, Agent, or Firm—Theodore Allen; Mark Casey

(57) ABSTRACT

Methods and systems for identifying a virus in breast ducts are provided. In addition, antiviral therapy for treating a virally infected breast duct is also provided. Patients with a viral infection identified in the breast ducts may be at risk for developing breast precancer or cancer.

15 Claims, 1 Drawing Sheet

OTHER PUBLICATIONS

K.M. Lau, "Expresion of estrogen receptor (ER)-alpha and ER-beta in normal and malignant prostatic epithelial cells: regulation by methylation and involvement in growth regulation", Cancer Research, Jun. 15, 2000, 60(12), pp. 3175-3182, Abstract Only.

A. Vilain et al., "DNA methylation and chromosome instability in breast cancer cell lines", FEBS Lett, Oct. 29, 1999, 460(2), pp. 231-234, Abstract Only.

S. M. Sirchia et al., "Evidence of epigenetic changes affecting the chromatin state of the retinoic acid receptor beta2 promoter in breast cancer cells", Oncogene, Mar. 16, 2000. 19(12), pp. 1556-1563, Abstract Only.

S. Milutinovic et al., "DNA Methyltransferase inhibition induces the transcription of the tumor suppressor p21(WAF1/CIP1/sdi1)", J. Biological Chem., Mar. 3, 2000, 275(9), pp. 6353-6359, Abstract Only.

P.M. Warnecke et al., "Cytosine methylation and human cancer", Curr. Opin. Oncol, Jan. 2000, 12(1), pp. 68-73, Abstract Only.

J. Song et al., "Chemopreventive effects of dietary folate on intestinal polyps in Apc+/−Msh2−/−− mice", Cancer Research, Jun. 15, 2000, 60(12), pp. 3191-3199, Abstract Only.

Y. NIWA et al, "BRCA1 Expression Status in Relation to DNA Methylation of the BRCA1 Promoter Region in Sporadic Breast Cancers, " Jpn J. Cancer Research, May 2000 , 91(5), pp. 519-526, Abstract Only.

R.G. Lapidus et al., "The loss of estrogen and progesterone receptor gene expression in human breast cancer", J. Mammary Gland Biol. Neoplasia, Jan. 1998, 3(1), pp. 85-94, Abstract Only.

* cited by examiner

IDENTIFICATION OF VIRAL AGENTS IN BREAST DUCTS AND ANTIVIRAL THERAPY THEREFORE

Benefit of the Aug. 8, 2000, filing date of provisional application Serial No. 60/223,857 by the same inventor and entitled "Identification of Viral Agents in Breast Ducts and Antiviral Therapy Therefor" is hereby claimed. This provisional application is also hereby incorporated by reference.

BACKGROUND OF THE INVENTION

Viruses are believed to act as etiologic agents of some cancers. For example, human papilloma virus has long been linked epidemiologically to cervical cancer. See McPhee et al, *Pathophysiology of Disease* $3^{rd}$ *edition* 2000 (chapter 5, page 80) Lange Medical Books/McGraw Hill, New York, N.Y.; and see Manos et al, JAMA 1999; 281: 1605–1610. Other studies document that Papilloma virus is associated with an increased risk in getting breast cancer. Studies published in Haagensen et al, Ann Surg, 1951; 133:18–36 documented a 3.3 fold increase in risk; Pellettierre et al, Am J Clin Path; 1971; 55: 740–748 found a 7.4 fold increase in risk. Buhl-Jorgensen et al Surg. Gynecol Obstet 1968; 127:1307–1312; Kilgore et al Surg. Gynecol Obstet 1953; 96:649–660; and Moore et al Surg. Gynecol Obstet 1961; 112:153–158 document collectively an 8% incidence of carcinomas during a 16 year period after identifying papillomas. The serotypes of papilloma virus most often linked to cancer have recently been found to encode for proteins that can bind and inactivate host tumor suppressor gene products. In this situation, a causative gene is not necessarily introduced by the virus, but the viral genome is able to direct the inactivation of tumor suppressor gene products and thereby favor growth and proliferation as well as malignant potential. See McPhee et al, *Pathophysiology of Disease* $3^{rd}$ *edition* 2000 (chapter 5, page 80) Lange Medical Books/McGraw Hill, New York, N.Y. Additionally, Epstein-Barr virus has been implicated in lymphoma and breast adenocarcinoma.

It would be advantageous to identify viral agents in breast duct fluid of a patient in order to anticipate a breast precancer or cancer risk. Such identification can also provide guidance in selecting subsequent specific prophylactic and therapeutic treatments. The present invention provides these and other benefits.

SUMMARY OF THE INVENTION

An object of the invention is identifying patients having viral infection in a breast duct. Another object of the invention is identifying patients at risk for developing breast precancer or cancer.

In accordance with these and other objects, the invention provides a method for identifying a patient having an increased risk for developing breast precancer or breast cancer, said method comprising providing a ductal fluid sample from one duct of a breast of a patient, said fluid not mixed with ductal fluid from any other duct of the breast; and detecting a viral agent in the ductal fluid sample. The viral agent is selected from the group consisting of a whole virus, a portion of a virus, a viral protein, a viral nucleic acid, and a viral marker, in the sample.

An additional object of the invention is to treat a patient having a viral infection that places the patient at risk for developing breast precancer or cancer. Accordingly, the invention provides a method of treating a patient at risk for or having breast precancer or breast cancer comprising detecting a viral agent in a fluid sample collected from a breast duct; and delivering to the patient a composition comprising an antiviral agent specific for the detected viral agent. The antiviral agent can be delivered intraductally to a duct in which the viral agent is detected.

The invention also provides kits and systems for identifying a patient having an increased risk for developing breast precancer or breast cancer, said kit or system comprising a ductal access tool, and reagents and instructions for detecting a viral agent in ductal fluid collected using the tool. The invention also provides kits and systems for treating a patient having a breast precancer or breast cancer in which a viral agent is a component and is present in the affected duct, said kit or system comprising a ductal access tool for intraductal delivery of a composition, the composition comprising an antiviral agent, and instructions for use.

DETAILED DESCRIPTION OF PREFERRED EMBODIMENTS OF THE INVENTION

Figure 1:
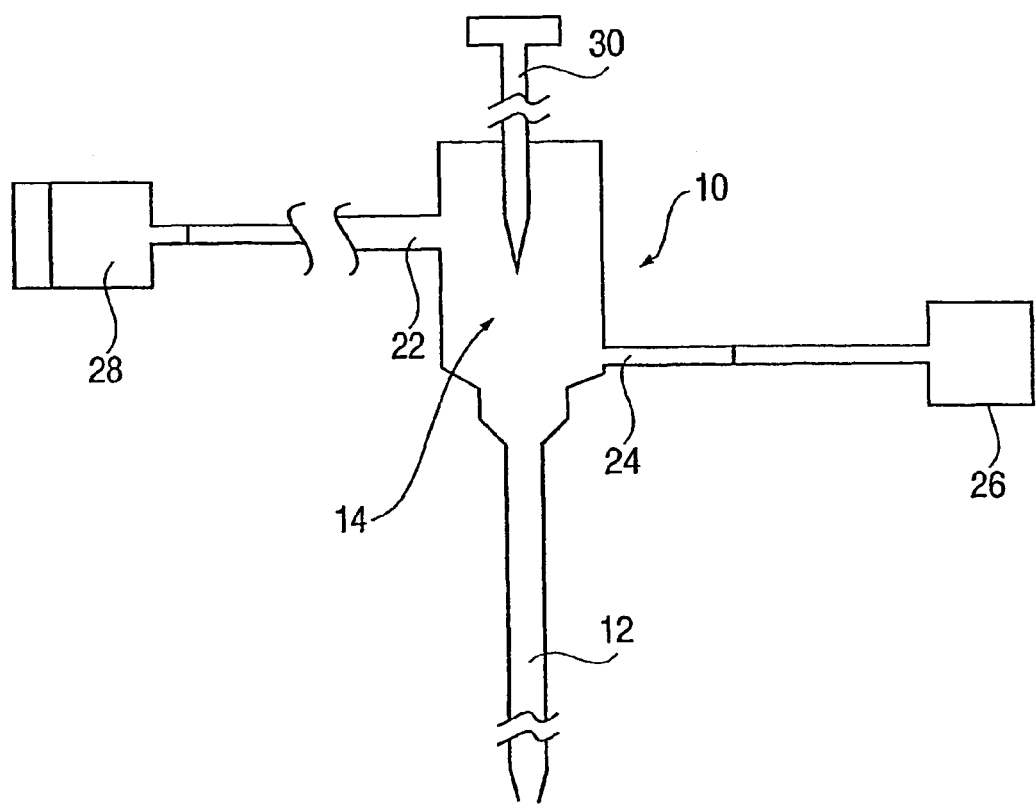
FIG. 1 illustrates a tool for accessing a breast duct according to the present invention.

The following preferred embodiments and examples are offered by way of illustration and not by way of limitation.

It is a discovery of the present invention that breast precancer and cancer of viral etiology have detectable virus, including e.g. whole virus, viral agents, viral markers, and/or gene products of a viral genome. In addition, the virus can be detected in the breast duct fluid of a patient having breast precancer or cancer of viral etiology. The usefulness of detecting a virus that may contribute to the onset of neoplasia includes identifying a risk factor for breast cancer or precancer. Viral detection is also useful to tailor prophylactic and/or therapeutic treatments in order to prevent or treat a breast precancer or cancer of viral etiology. Viral detection may also be used to monitor the success of an anti-viral, an anti-cancer therapy, and/or an anti-precancer therapy.

The virus may be detected systemically in blood or sera of a patient. The virus may also be detected locally in the breast in ductal fluid obtained from a breast duct. Breast cancers are believed to originate in one or more of the 6–9 breast ducts of a human breast. Breast duct fluid can be retrieved from patients through nipple aspiration or ductal lavage. The latter provides an opportunity to identify a specific high risk duct and/or to target treatment to the identified at risk duct.

The method is practiced by providing a ductal fluid sample from at least one duct of a breast of the patient. Providing the ductal fluid sample can comprise obtaining the sample from the breast. Providing the ductal fluid sample can also comprise receiving a sample that had been previously obtained. For example, a laboratory can receive a ductal fluid sample from a patient or a practitioner, and the laboratory can be directed to make an analysis of the sample. Where the fluid is obtained from the breast, the fluid sample can be obtained e.g. by nipple aspiration of the milk ducts or by ductal lavage of at least one breast milk duct. When fluid is collected by ductal lavage, the fluid can be collected from a single duct. For example the duct and the collection tube can be marked so that the analysis of the fluid is traceable to the accessed duct.

The ductal epithelial cells can be derived from any part of the breast milk duct, including, e.g. the ductal lumen and/or the terminal ductal lobular unit (TDLU). Cells derived from the ductal lumen may comprise any of stages of neoplasia or pre-neoplasia or normal cells, including, e.g. benign, hyperplastic, atypical, in situ carcinoma, and invasive carcinoma. Cells derived from the TDLU may also have similar stages as found in other lumenal ductal epithelial cells not from the TDLU including, e.g. hyperplasia, atypia, in situ carcinoma, and invasive carcinoma. For both the lumenal ductal epithelial cells, and the TDLU epithelial cells the category terms such as normal, mild atypia, marked atypia, premalignant, and malignant also can apply depending on the convention of terminology adopted by the practitioner or cytologist, etc.

Nipple aspiration of breast ductal fluid is achieved by using vacuum pressure. Nipple aspiration techniques are also described and claimed in co-pending and co-owned patent application U.S. Ser. No. 09/438,219, herein incorporated by reference in their entirety. Nipple aspirate fluid can be retrieved as described in e.g. Goodson W H & King E B, *Chapter 4: Discharges and Secretions of the Nipple*, The Breast: comprehensive Management of Benign and Malignant Diseases (1998) $2^{nd}$ Ed. vol 2, Bland & Kirby eds. W. B. Saunders Co, Philadelphia, Pa. pp. 51–74; Wrensch et al., (1992) American Journal of Epidemiology. 135(2):130–41; and Sauter et al (1997) British Journal of Cancer. 76(4):494–501; aspirating the nipple can also be achieved as described in Petrakis (1993) *Cancer Epidem. Biomarker Prev.* 2:3–10, Petrakis (1986) *Breast Cancer Res. Treat* 8: 7–19, Wrensch et al (1992) *Am. J. Epidem.* 135: 130–141, Wrensch et al (1990) *Breast Cancer Res Treat* 15: 39–21, and Wrensch et al (1989) *Cancer Res.* 49: 2168–2174. Fluid secretions from the nipple can be collected as they spontaneously appear on the nipple surface. In order to collect the fluid not mixed with ductal fluid from other ducts, a practitioner carefully watches for the signs of fluid and retrieves the fluid from the nipple surface near the orifice before it has a chance to mix with fluid from any other orifice.

The ductal fluid can be retrieved by placing a ductal access tool in the duct and infusing fluid into the duct through the tool and retrieving from the accessed duct through the tool a portion of the infused fluid mixed with ductal fluid. The process may be repeated for more than one duct on a breast, and/or the process can be repeated for a plurality of ducts on a breast. Either sequential or simultaneous access of the duct on a breast can be used. By the procedure of ductal lavage, ductal epithelial cells that line the walls of the ductal lumen or resided in the TDLU are washed out of the duct. Lavage or wash fluid is infused into the duct, and the lavage fluid mixed with ductal fluid is collected. Lavage is described in copending and co-owned applications including Ser. Nos. 09/067,661, 09/301,058, PCT US99/09141, Ser. Nos. 60/122,076, 09/313,463, 60/143,359, and U.S. Ser. No. 09/473,510, all incorporated by reference in their entirety. In some cases suction can be applied to the tool accessing the ductal lumen in order to retrieve a maximum amount of cells and/or fluid. Lavage or wash fluid can be infused into the duct, and collected. In general, ductal fluid can be retrieved by a medical tool, e.g. a catheter, cannula, or stent, placed into the duct to infuse wash fluid and to retrieve a mixture of wash and ductal material. The fluid from the breast duct can contain ductal epithelial cells, including cells of a stage considered to be precancerous or cancerous.

Additionally, the ductal fluid may be analyzed in situ, i.e. inside the breast and inside the breast duct, e.g. where a viral marker or other indicia of viral presence in the duct can be identified from within the breast. Methods of in situ analysis can include use of such molecular biology tools, methods, and materials as described in e.g. U.S. Pat. Nos. 5,169,774, 5,720,937, 5,677,171, 5,720,954, 5,725,856, 5,770,195, and 5,772,997.

The virus may be detected in any form. For example, the virus may be detected whole, or a protein or polypeptide of the virus (e.g. a viral coat protein or other protein antigen made by the virus or associated with the virus) or a nucleic acid molecule or sequence (e.g. DNA or RNA encoding a viral protein or polypeptide or having other function in the lifecycle of the virus) may be detected. In addition, any other suitable and reliable viral marker associated with the virus sought may be detected. The virus (or viral protein, polypeptide, nucleic acid or other viral marker) can be detected by standard means such as described in Sambrook et al., Molecular Cloning: A Laboratory Manual, $2^{nd}$ Ed. (Cold Spring Harbor Press, Cold Spring Harbor, N.Y. 1989), or other standard protocols. Protocols and assays can include, e.g. antigen-antibody binding assays, other binding assays, capture assays, filtration, chromatography, polymerase chain reactions, southern blots, northern blots, western blots, ELISA, immunohistochemistry, and assays which are in particular specific for viral detection or detection of viral gene products or nucleic acids present in a virus, and the like. Such assays are standard in the art.

Ductal epithelial cells retrieved by nipple aspiration or ductal lavage may be analyzed as described for viral infection and also, in addition may be analyzed for morphological abnormality by cytological analysis. Once the ductal fluid is analyzed for one or more markers, the fluid may also be analyzed cytologically to determine the cytological status of the ductal epithelial cells and other cells. Cytological assays that can be performed on the cells retrieved from a duct or from nipple aspirate can include e.g. assays described in King et al, *J. Nat'l Cancer Inst* (1983) 71:1115–21, Wrensch et al. (1992) *Am. J. Epidem.* 135: 130–141, Papanicolaou et al, (1958) *Cancer,* 11:377–409 and Goodson W H & King E B, *Chapter 4: Discharges and Secretions of the Nipple*, THE BREAST: COMPREHENSIVE MANAGEMENT OF BENIGN AND MALIGNANT DISEASES (1998) $2^{nd}$ Ed. vol 2, Bland & Kirby eds. W. B. Saunders Co, Philadelphia, Pa. pp. 51–74. For example, as described in Goodson and King (page 60) atypical hyperplasia presents as having cellular abnormalities, increased coarseness of the chromatin, and tendency for more single cells as well as groups of cells. With regard to carcinoma in situ, Papanicolaou et al., described cellular abnormalities, e.g. nuclear abnormalities diagnosed by cytology of fluid from nipple secretions containing ductal cells. The cytology of abnormal cells can also be conducted as described in Sartorius et al (1977) *J. Natl Cancer Inst* 59: 1073–1080, and King et al, (1983) *JNCI* 71(6) 1115–1121. Atypia and carcinoma in situ are widely characterized pathologically, as described in Page et al, (1998) *Mod Pathol* 11(2): 120–8. The ductal fluid can be analyzed by cytological techniques by placing some of the fluid on a slide with a standard cytological stain using a light microscope. The cells can be studied for atypical growth patterns in individual cells and clusters of cells using published methods, including Mouriquand J, (1993) S Karger Pub, "Diagnosis of Non-Palpable Breast Lesions: Ultrasonographically Controlled Fine-Needle Aspiration: Diagnostic and Prognostic Implications of Cytology" (ISBN 3805557477); Kline T S and I K, Pub Igaku-Shoin Medical "Breast: Guides to Clinical Aspiration Biopsy" (LSBN 0896401596; Masood, *American Society of Clinical Pathology*: November 199S, "Cytopathology of the Breast" ISBN 0891893806; and Feldman P S, *American Society of Clinical Pathology*, November 1984, "Fine Needle Aspiration Cytology and Its Clinical Applications: Breast and Lung" ISBN 0891891846.

Other references that discuss cytological analysis and which give guidance to an analysis of ductal epithelial cells derived from ductal fluid include Silverman et al, (Can FNA biopsy separate atypical hyperplasia, carcinoma in situ, and invasive carcinoma of the breast?: Cytomorphologic criteria and limitations in diagnosis, Diagnostic Cytopathology) 9(6):713–28, 1993; Masood et al, (Immunohistochemical differentiation of atypical hyperplasia vs. carcinoma in situ of the breast) *Cancer Detection & Prevention.* 16(4):225–35, 1992; Masood et al, (Cytologic differentiation between proliferative and nonproliferative breast disease in mammographically guided fine-needle aspirates) *Diagnostic Cytopathology.*7(6):581–90, 1991; Masood S., (Occult breast lesions and aspiration biopsy: a new challenge) Diagnostic Cytopathology. 9(6):613–4, 1993; Masood S., (Prognostic factors in breast cancer: use of cytologic preparations) *Diagnostic Cytopathology.* 13(5): 388–95, 1995; Novak and Masood, (Nuclear grooves in fine-needle aspiration biopsies of breast lesions: do they have any significance? *Diagnostic Cytopathology.* 18(5): 333–7, 1998; Sidawy et al, (Interobserver variability in the classification of proliferative breast lesions by fine-needle aspiration: results of the Papanicolaou Society of Cytopathology Study) *Diagnostic Cytopathology.* 18(2):150–65, 1998; Masood et al, (Automation in cytology: a survey conducted by the New Technology Task Force, Papanicolaou Society of Cytopathology) *Diagnostic Cytopathology.* 18(1):47–55, 1998; and Frykberg and Masood Copeland E M 3d. Bland K I., (Ductal carcinoma in situ of the breast) *Surgery, Gynecology & Obstetrics* 177(4):425–40, 1993.

The cytological categories of ductal epithelial cells can be distinguished by any one or more of the following descriptors as follows: normal, abnormal, hyperplasia, atypia, ductal carcinoma, ductal carcinoma in situ (DCIS), ductal carcinoma in situ—low grade (DCIS-LG), ductal carcinoma in situ—high grade (DCIS-HG), invasive carcinoma, atypical mild changes, atypical marked changes, atypical ductal hyperplasia (ADH), insufficient cellular material for diagnosis, and sufficient cellular material for diagnosis. These categories classify the epithelial cells drawn from the breast duct lumen or TDLU cytologically, and these classifications may indicate either cancer or its precursors, or absence of cancer indicia. Other markers in addition to the cell morphology may be capable of differentiating between any two of cytological categories listed.

In addition, collected ductal fluid comprising molecular and cellular material can be analyzed, e.g. as described or suggested herein. Thus, once the ductal fluid sample is retrieved from the breast it can also be examined for the presence of a marker such as, for example a protein, a polypeptide, a peptide, a nucleic acid, a polynucleotide, an mRNA, a small organic molecule, a lipid, a fat, a glycoprotein, a glycopeptide, a carbohydrate, an oligosaccharide, and a chromosomal abnormality, a whole cell having a marker molecule, a particle, a secreted molecule, an intracellular molecule, and a complex of a plurality of molecules as described above. In addition, the marker may be capable of differentiating between any two of cytological categories listed herein. The different categories of markers are tested differently depending on the category and possibly also on the location of the marker in the cell (for example, a cell surface protein might be detected differently than a cytoplasmic or nuclear protein). Typically, assays comprising one or more of binding, coloration, precipitation, affinity column selection, in-situ binding, solution phase binding, nucleic acid probe labeling, protein probe labeling, polypeptide probe labeling, peptide probe labeling, and/or a combination or variation of these processes can be used. Standard procedure for conducting such assays generally (e.g. ELISA, RNA or DNA probe hybridization, and other binding or other detection assays) are described in Sambrook et al., Molecular Cloning: A Laboratory Manual, $2^{nd}$ Ed. (Cold Spring Harbor Press, Cold Spring Harbor, N.Y. 1989). Additionally, the marker may assist in evaluating the viral infection: either in determining which viral agent has infected the cells, or determining the extent of the infection, or the damage or causative, or quasi-causative effect of the virus on the neoplastic or preneoplastic status of the epithelial cells in the breast duct and/or TDLU.

A patient may fall into one of several categories after analysis of viral content in the ductal fluid and cytological analysis of the ductal epithelial cells, and/or in addition analysis of any markers also found in the ductal fluid. Monitoring the patient can be accomplished at any appropriate interval. The interval may be selected based on such information as the amount of viral infection, and/or level or stage of cytological abnormality. Appropriate intervals may include, e.g. weekly, biweekly, monthly, bimonthly, every six months, and annually, etc. The following table is illustrative.

| Patient | Virus | Cytology | Conclusion/Treatment |
| --- | --- | --- | --- |
| A | Neg | Normal | No viral infection<br>Low risk precancer or cancer; benign cells |
| B | Positive (low or high titer) | Normal | High risk; stratify by titer; which virus? Treatment: consider administration of an antiviral agent; monitor ductal fluid for effectiveness of AV treatment and/or non-benign cytological findings |
| C | Positive (low or high titer) | Hyperplasia | Consider anti-viral treatment and prophylaxis for precancer or cancer; monitor for reduction in viral load |
| D | Positive | Atypia (low grade) | Consider anti-viral treatment and prophylaxis for cancer and/or therapeutic treatment for precancer; monitor for reduction in viral load |
| E | Positive | Atypia (high grade) | Consider anti-viral treatment and surgery and/or therapeutic treatment for precancer or cancer; monitor for reduction in viral load |
| F | Positive | Malignant | Consider anti-viral treatment and surgery and/or therapeutic treatment for cancer and/or anti-metastatic treatment also; monitor for reduction in viral load |

Antiviral agents will be directed towards the infecting virus and can include in general any anti-viral agent capable of reducing a viral titer or a concentration of a viral marker or the effectiveness of the virus or an agent of the virus. Thus, an anti-viral agent can be e.g. an anti-papilloma viral agent, an anti-epstein-Barr viral agent, or the like. For human papilloma virus (HPV) exemplary anti-viral agents include, e.g. interferon (including alpha, beta and/or gamma interferons), imidazoquinolinamine derivatives (e.g. imiquimod), cytokines, and cidofovir. Antiviral agents against Epstein-Barr viral infection (EBV) can include agents and therapeutic approaches listed in Okano, Pediatr Hematol Oncol 1997; 14(2): 109–119; also potentially useful are anti-herpes virus drugs such as nucleoside analogs or their prodrugs, phosphorylated nucleoside (nucleotide), penciclovir, famciclovir, valaciclovir, and lobucavir, and other agents as described in Alrabiah and Sacks, Drugs 1996, 52(1): 17–32.

Prophylactic and therapeutic agents can include e.g. agents disclosed in U.S. Pat. No. 5,763,415. Some breast cancers or precancers may be responsive to administration with some form of estrogen activity modulator. See Howell et al (1998) *Recent Results Cancer Res* 152:227–244 ("The Primary use of Endocrine Therapies") To reduce the cancer, the patient is administered an agent that blocks estrogen activity, either by modulating estrogen, its receptor, or by blocking estrogen synthesis. An estrogen activity modulator can comprise a class of agents selected from the group consisting of a selective estrogen receptor modulator (SERM), an estrogen antagonist, and a modulator of estrogen synthesis. The estrogen activity modulator can be tamoxifen, raloxifene, EM 800, droloxifene, ioxdroxifene, RU 39411, RU 58668, ICI 164384, faslodex, soy, a soy isoflavone, a gonadotropin releasing hormone agonist, or an aromatase inhibitor. The soy isoflavone can be genistein or daidzein. The aromatase inhibitor can be toremifene.

Some possible candidate estrogen activity modulators are described in el Khissiin and Leclercq, (1998) *Steroids* 63(11): 565–74; O'Regan et al (1998) *J Nat'l Cancer Inst* 90(20): 1552–8; Favoni and Cupis (1998) *Trends Pharmacol Sci* 19(10): 406–15; Williams, GM (1998) *J Nat'l Cancer Inst* 90:1671; Huynh et al (1996) *Clin Cancer Res* 2:2037–2042; England and Jordan (1997) *Oncol Res* 9:397–402; Ashby et al (1997) *Regul Toxicol Pharmacol* 25:226–3 1, Long et al, (1998) J Steroid Biochem Mol Biol 67:293–304. In addition, estrogen activity modulators obtained from plants or foods can be used, including soy and soy isoflavones, including genistein and daidzein, as described in Xu et al (1998) *Cancer Epidemiol Biomarkers Prev* 7:1101–8, Charland et al (1998) *Int J Mol Med* 2:225–228, Franke et al (1998) *Am J Clin Nutr* 68:1466S–1473S, Kim et al (1998) *Am J Clin Nutr* 68: 1418S–1425S, Shao et al (1998) *Cancer Res* 58:4851–7, Shao et al, *Journal of Cellular Biochemistry* 69(1):44–54, 1998; Liggins et al (1998) Anal Biochem 264:1–7, Kinoshita et al (1998) *Adv Exp Med Biol* 439: 1178–29, and Dees and Kennedy (1998) *Curr Opin Oncol* 10(6):5 17–522. Estrogen activity modulators that are aromatase inhibitors are described in Mor et al (1998) *J Steroid Biochem Mol Biol* 67(5–6):403–411; Goss et al (1999) *Oncotogy* 56(2): 114–121; Coombes (1998) *Recent Results Cancer Res* 152: 277–84; Costa et al (1999) *Cancer* 85:100–3; Long et al (1998) *J Steroid Biochem Mol Biol* 67(4): 293–304; and Lamb and Adkins (1998) *Drugs* 56(6):1 125–40. Gonadotropin hormone releasing agonists (GnRHA) are described at website having the following web address: "_amaassn.org/special/womh/newsline/reuters/03315440.htm_"(date Apr. 5, 1999); and in other publications including Jonat (1998) *Br J Cancer* 78 Suppl 4:5–8; Szamel et al (1998) *Cancer Chemother Pharmacol* 42(3):241–6; Ciardo et al (1998) *Minerva Ginecol* 50(1–2):25–29; Nagy et al (1996) *Proc Natl Acad Sci USA* 93(14):7269–73; Burger et al (1996) *Eur J Obstet Gynecol Reprod Biol* 67(1):27–33.

The administration of anti-viral and/or therapeutic or prophylactic agents can be systemic or local (e.g. intraductal). Intraductal administration (local) is accomplished by accessing the duct or ducts affected with a ductal access tool 10 (discussed below), a catheter, cannula or stent or similar tool, and infusing active agent into the duct. The agent may be formulated in a particular composition, e.g. a liquid or gel, or other composition appropriate for infusion into a breast duct. Local intraductal administration is also described in U.S. Ser. No. 09/313,463 filed May 17, 1999, U.S. Ser. No. 09/502,206 filed Feb. 10, 2000, and U.S. Ser. No. 09/506,477 filed Feb. 29, 2000, hereby incorporated by reference.

Dosage and choice of antiviral agent can be affected by such parameters as viral titer of the initially detected virus, or other quantitation of the viral infection or viral load, and which type of virus is the infecting agent. Viral titer or other indicia of viral load may be monitored prophylactically to reduce cancer risk in patients without identified cellular abnormality, or with only hyperplasia or mild atypia. Likewise dosage of prophylactic or therapeutic agent can be selected based on whether precancer or cancer is detected and the grade of abnormality of the cells and/or number of ducts affected and/or age of the patient, etc.

The invention also provides a kit or system identifying and/or treating the patients and/or conditions described herein. Accordingly, a kit or system is provided for identifying a patient having an increased risk for developing breast precancer or breast cancer. The kit or system comprises a ductal access tool 10, and reagents and instructions for detecting a viral agent in ductal fluid collected using the tool, e.g. the reagents provide for detection of the virus, or retrieval of the ductal fluid containing the virus, and the instructions provide guidance for practicing the methods described herein. A kit or system for treating a patient at risk for or having a breast precancer or breast cancer in which a viral agent is a component and is present in the affected duct comprises the ductal access tool 10 for intraductal delivery of a composition (e.g. a catheter, cannula, stent or the like) and a composition comprising an antiviral agent (such as those described herein), and instructions for use of the tools and antiviral agent. The instructions can include, e.g. guidance as to the choice of antiviral agent, dosage, administration method (e.g. as described herein), monitoring of the treatment progress, and/or other guidance for completing an effective treatment protocol.

FIG. 1 illustrates an example of the ductal access tool 10 used to access a breast duct. The tool 10 can administer or infuse fluid into the duct. Additionally, tool 10 can collect breast duct fluid from within the duct. The tool 10 comprises an elongated single lumen 12 for positioning within the breast duct and infusing and collecting fluid from within the breast duct. The tool 10 also includes a fluid infusion and collection hub 14 that is in fluid communication with the lumen 12. The hub 14 includes an infusion port 24 through which fluid from reservoir 26 is introduced into the hub 14, the lumen 12 and eventually the breast duct. The hub 14 also comprises a collection port 22 that is connected to a collection receptacle 28. Reservoir 26 and receptacle 28 can each comprise a syringe or other well-known fluid carrying container. A probe (dialtor) 30 can be used to introduce the lumen 12 into the breast duct or locate a ductal opening.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for identifying a patient having an increased risk for developing breast precancer or breast cancer, said method comprising the following steps:
   (a) introducing a ductal access tool into a breast duct, said access tool comprising single elongated lumen;
   (b) introducing a fluid into the breast duct through said elongated lumen;
   (c) retrieving a ductal fluid sample from within the breast duct through said lumen, said ductal fluid being free of any ductal fluid from another duct of the breast; and
   (d) detecting a viral agent in the ductal fluid sample.

2. A method as in claim 1, wherein the viral agent is selected from the group consisting of a whole virus, a portion of a virus, a viral protein, a viral nucleic acid, and a viral marker, in the sample.

3. A method as in claim 1, wherein, steps (a)–(d) of the method are repeated for a plurality of breast ducts.

4. A method as in claim 1, further comprising analyzing the ductal fluid for abnormal cytology.

5. A method as in claim 1, wherein a viral agent is detected, and further comprising the steps of: periodically repeating steps (a)–(c); and monitoring a variable selected from the group consisting of a viral titer, concentration of a viral agent, and presence of a viral marker in the ductal fluid samples.

6. A method as in claim 5, wherein the viral agent is monitored and the viral agent is selected from the group consisting of a whole virus, a portion of a virus, a viral protein, a viral nucleic acid, and a viral marker by taking repeated periodic ductal fluid samplings.

7. A method as in claim 5, wherein the periodicity is selected from the group consisting of daily, weekly, biweekly, monthly, bimonthly, every six months, annually, and biannually.

8. A method as in claim 1, wherein the viral agent is selected from the group consisting of papilloma virus, Epstein-barr virus, and herpes virus.

9. A method of treating a patient at risk for or having a breast precancer or breast cancer, said method comprising the following steps:
   (a) introducing a ductal access tool into a breast duct, said access tool comprising a single elongated lumen;
   (b) introducing a fluid into the breast duct through said elongated lumen;
   (c) retrieving a ductal fluid sample from within the breast duct through said lumen;
   (d) detecting a viral agent in the retrieved ductal fluid sample from the breast duct; and
   (e) delivering to the patient a composition comprising an antiviral agent specific for the detected viral agent.

10. A method as in claim 9, wherein the viral agent is selected from the group consisting of a whole virus, a portion of a virus, a viral protein, a viral nucleic acid, and a viral marker.

11. A method as in claim 9, wherein the antiviral agent is delivered intraductally to the breast duct in which the viral agent has been detected.

12. A method as in claim 9, further comprising repeating steps (a)–(c) for a plurality of additional breast ducts; and wherein a viral agent is detected in at least one of the fluid samples separately retrieved from the plurality of additional breast ducts.

13. A method as in claim 9, wherein the viral agent is selected from the group consisting of papilloma virus, Epstein-barr virus, and herpes virus.

14. A method as in claim 9, wherein the antiviral agent is selected from the group consisting of an anti-HPV viral agent, and anti-EBV viral agent, and an anti-herpes viral agent.

15. A method as in claim 9, wherein said delivering step includes delivering the composition comprising said antiviral agent systemically.

* * * * *